United States Patent [19]

Gervais

[11] Patent Number: 4,739,061
[45] Date of Patent: Apr. 19, 1988

[54] PROCESS FOR PREPARING N-METHYL DERIVATIVES OF METHYL DIHYDROLYSERGATE AND METHYL METHOXYLUMILYSERGATE

[75] Inventor: Christian Gervais, Villeurbanne, France

[73] Assignee: Rhone-Poulenc Sante, Courbevoie, France

[21] Appl. No.: 884,036

[22] Filed: Jul. 10, 1986

[30] Foreign Application Priority Data

Jul. 11, 1985 [FR] France ................ 85 10622

[51] Int. Cl.$^4$ .......................... C07D 457/04
[52] U.S. Cl. .......................... 546/69; 546/67
[58] Field of Search .............. 546/67, 68, 69; 548/469

[56] References Cited

U.S. PATENT DOCUMENTS

| | | | |
|---|---|---|---|
| 3,113,133 | 12/1963 | Hofmann et al. | 546/69 |
| 3,228,940 | 1/1966 | Bosisio et al. | 546/67 |
| 3,228,941 | 1/1966 | Bernardi et al. | 546/67 |
| 3,228,943 | 1/1966 | Bernardi et al. | 546/68 |
| 3,879,554 | 4/1975 | Temperilli | 546/69 |
| 4,230,859 | 10/1980 | Rucman | 546/69 |
| 4,232,157 | 11/1980 | Enrico | 546/68 |

FOREIGN PATENT DOCUMENTS

| | | | |
|---|---|---|---|
| 634886 | 7/1963 | Belgium . | |
| 753635 | 1/1971 | Belgium | 546/67 |
| 0000533 | 7/1979 | European Pat. Off. . | |
| 24820 | 11/1964 | Japan | 546/67 |
| 2013194 | 8/1979 | United Kingdom | 546/67 |

OTHER PUBLICATIONS

Erico, CA 93-150450f.
Troxler et al., Helv. Chem. Acta, 40, 1721, (1957).
Societa Farmaceutici Italia, CA; vol. 61, (1964), 1907a.
Barry et al., CA 98-197579y, (1983).

*Primary Examiner*—Donald G. Daus
*Assistant Examiner*—Cecilia Shen
*Attorney, Agent, or Firm*—Stevens, Davis, Miller & Mosher

[57] ABSTRACT

A process for preparing an N-methyl derivative of methyl dihydrolysergate and methyl methoxylumilysergate, of formula:

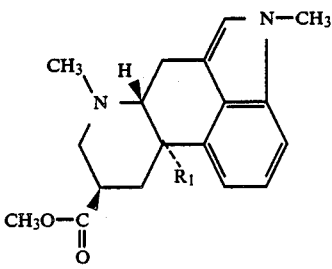

in which $R_1$ denotes a hydrogen atom or a methoxy group, which comprises reacting a methylating agent with a compound of formula:

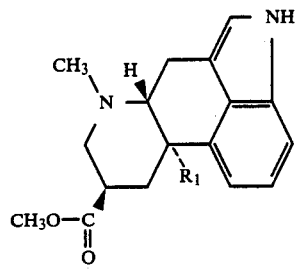

in which $R_1$ is defined as above, in the presence of a quaternary salt, in the presence of a solid metal alcoholate of formula $CH_3$—OM in which M denotes an alkali metal atom, or an alkali metal hydride, and in the presence of a dehydrating agent of formula $R_2$—COO—$CH_3$ in which $R_2$ denotes a hydrogen atom or an alkyl, alkyloxy, alkyloxycarbonyl or aryl group or of formula $R_3$—$C(OCH_3)_3$ in which $R_3$ denotes a hydrogen atom, an alkyl group or an aryl group.

5 Claims, No Drawings

PROCESS FOR PREPARING N-METHYL DERIVATIVES OF METHYL DIHYDROLYSERGATE AND METHYL METHOXYLUMILYSERGATE

The present invention relates to preparing N-methyl derivatives of methyl dihydrolysergate and methyl methoxylumilysergate.

These N-methyl derivates are useful intermediates in the synthesis of pharmaceutical products described in U.S. Pat. No. 3,228,943.

The prior art teaches that the methylation of the indole nitrogen atom of ergoline derivatives must be carried out using a methylating agent such as a methyl halide or methyl sulphate, in the presence of a base such as potassium amide in liquid ammonia, according to F. Troxler, Helv. Chim. Acta, 40, 1721 (1957) or sodium amide in liquid ammonia, according to Swiss Pat. No. 386,441 or U.S. Pat. No. 3,113,133. These processes require the use of sodium or potassium and the maintenance of a temperature in the region of $-40°$ C. which, from the industrial standpoint, involves considerable financial investment. Furthermore, these processes can lead to by-products of methylation.

European Patent Application No. 553 describes the methylation of methyl lumilysergate in the presence of 45% strength sodium hydroxide which is used in liquid/liquid phase transfer catalysis. Such a reaction has to be carefully controlled to avoid saponification of the methyl ester group.

European Patent Application No. 4664 describes the methylation of 10α-methoxylumilysergol in the presence of solid potassium hydroxide in dimethyl sulphoxide, but the reaction is not selective and a substantial proportion of methyl ether is formed from the primary alcohol group.

It is known to methylate an unsubstituted indole in the presence of sodium hydride in hexamethylphosphorotriamide (See G. H. Rubottom and J. C. Chabala, Synthesis, 566 (1973)) or sodium amide, lithium amide or ethylmagnesium bromide in tetrahydrofuran, ether, benzene or hexamethylphosphorotriamide (M. G. Reinecke et al., J. Org. Chem., 37 (20) 3066 (1972)).

The present invention provides a process for preparing an N-methyl derivative of methyl dihydrolysergate or methyl methoxylumilysergate of formula:

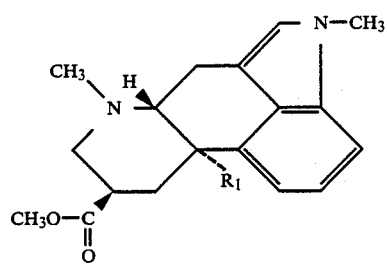

in which $R_1$ denotes a hydrogen atom or a methoxy radical which comprises reacting a methylating agent with a compound of formula:

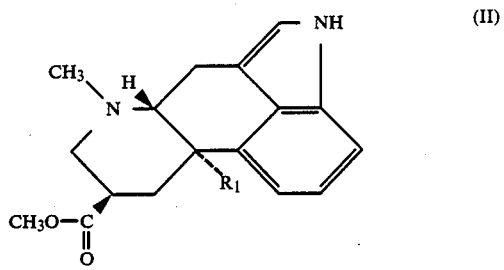

in which $R_1$ is defined as above, in the presence of, as liquid/solid phase transfer catalyst, a quaternary salt, in the presence of, as base, a solid metal alcoholate of general formula $CH_3-OM$ (III) in which M denotes an alkali metal atom, e.g. a sodium or potassium atom, or an alkali metal hydride, and in the presence of a dehydrating agent of formula $R_2-COO-CH_3$ (IV) in which $R_2$ denotes a hydrogen atom or an alkyl, alkyloxy, alkyloxycarbonyl or aryl group or of formula $R_3-C(OCH_3)_3$ (V) in which $R_3$ denotes a hydrogen atom, an alkyl group or an aryl group.

In the process according to the invention, the methylating agent can be used in the presence of a liquid/solid phase transfer catalyst in combination with a dehydrating agent of formula (IV) or (V), and in the presence of a non-transesterifying base.

The process is generally carried out at a temperature of from $-10°$ to $80°$ C., and it does not have to make use of special technology.

Moreoever, the use of a dehydrating agent of formula (IV) or (V) enables the extraneous saponification reaction to be controlled, even in the presence of traces of water present in the reagents.

In general, the process according to the invention is carried out in a aprotic organic solvent, for example an ether such as tetrahydrofuran, dioxane or 1,2-dimethoxyethane, diethyl ether, diisopropyl ether, dibutyl ether or methyl tert-butyl ether, an ester such as methyl acetate, methyl propionate, methyl carbonate, methyl formate, methyl benzoate or methyl orthoformate, or a nitrile such as acetonitrile, or mixtures thereof.

The dehydrating agent can be, for example, an ester such as methyl formate, methyl acetate, methyl benzoate, methyl carbonate, methyl oxalate or methyl orthoformate. It is also possible to have a co-dehydrating agent such as magnesium or dimethoxymagnesium. The dehydrating agents can be used as solvents.

The liquid/solid phase transfer catalyst in generally a quaternary ammonium salt such as tetraalkylammonium halide or sulphate, e.g. tetrabutylammonium chloride or a phosphonium salt.

The base is generally an alkali metal alcoholate, e.g. sodium or potassium methylate or tert-butylate, or an alkali metal hydride such as sodium or potassium hydride.

The methylating agent is generally a methyl halide, methyl sulphate, methyl methanesulphonate, methyl p-toluenesulphonate or methyl phosphate.

With respect to the compoiunds to be methylated, an excess of base is generally used in a mole ratio of from 1:2 to 1:10, an excess of dehydrating agent of formula (IV) or (V) is generally used in a mole ratio of from 1:1 to 1:500 and the phase transfer catalyst is generally used in a mole ratio of from 1:0.05 to 1:2. It is especially advantageous to use a slight excess of methylating agent.

The compounds of formula (I) can be isolated from the reaction mixture by customary techniques.

The following examples show how the invention can be put into practice.

EXAMPLE 1

Methyl 10α-methoxylumilysergate (1.758 g; 5.6 mmol), anhydrous tetrahydrofuran (115 cc), methyl benzoate (15 cc; 120.5 mmol) and tetrabutylammonium chloride (1.574 g; 5.6 mmol) were introduced into a reactor which was maintained shielded from moisture. After complete dissolution, powdered sodium methylate (2.5 g; 46.3 mmol) was introduced with stirring. After 5 minutes' stirring, a solution of dimethyl sulphate (0.776 g; 6.16 mmol) in anhydrous tetrahydrofuran was introduced over 5 hours.

The reaction mixture was poured into 0.65N sulphuric acid (86 cc) maintained at 0° C. The aqueous phase (pH 2) was washed with ethyl acetate (35 cc), alkalinized to pH 9 by adding ammonia solution and then extracted with ethyl acetate (4×70 cc). The combined organic phases were dried. After evaporation of the solvent, methyl 10α-methoxy-1-methyllumilysergate was obtained in an 80–85% yield, the titer of which product, determined by high performance liquid chromatography and by acidimetry, was greater than 99%.

EXAMPLE 2

The procedure of Example 1 was repeated but using:
methyl 10α-methoxylumilysergate (0.314 g; 1 mmol)
methyl benzoate (51.5 g; 378.6 mmol)
tetrabutylammonium chloride (0.277 g; 1 mmol)
sodium methylate (0.432 g; 8 mmol) and
dimethyl sulphate (0.315 g; 2.5 mmol).

The dimethyl sulphate was added after the reaction mixture had been stirred for 17 hours at a temperature in the region of 20° C.

The degree of conversion of methyl 10α-methoxylumilysergate was 92%.

The yield of methyl 10α-methoxy-1-methyllumilysergate was 81%.

EXAMPLE 3

The procedure of Example 1 was repeated but using:
methyl 10α-methoxylumilysergate (0.314 g; 1 mmol)
a tetrahydrofuran/methyl acetate (1:1 by volume) mixture (11.1 cc) as solvent
tetrabutylammonium chloride (0.277 g; 1 mmol)
methyl acetate (7.4 g; 0.1 mol)
sodium methylate (0.432 g; 8 mmol) and
dimethyl sulphate (0.441 g; 0.0035 mmol).

The dimethyl sulphate was added after the reaction mixture had been stirred for 2 hours 20 minutes at a temperature in the region of 20° C.

The degree of conversion of methyl 10α-methoxylumilysergate was 92%.

The yield of methyl 10α-methoxy-1-methyllumilysergate was 80%.

EXAMPLE 4

The procedure of Example 1 was repeated but using:
methyl 10α-methoxylumilysergate (0.314 g; 1 mmol)
a tetrahydrofuran/methyl carbonate (1:1 by volume) mixture (22.2 cc) as solvent
tetrabutylammonium chloride (0.277 g; 1 mmol)
methyl carbonate (4.5 g; 50 mmol)
dimethoxymagnesium (0.11 g; 2 mmol)
sodium methylate (0.432 g; 8 mmol) and
dimethyl sulphate (0.167 g; 1.33 mmol).

The dimethyl sulphate was added after the reaction mixture had been stirred for 2 hours at a temperature in the region of 20° C.

The degree of conversion of methyl 10α-methoxylumilysergate was 93%.

The yield of methyl 10α-methoxy-1-methyllumilysergate was 82%.

I claim:

1. A process for preparing a compound of formula:

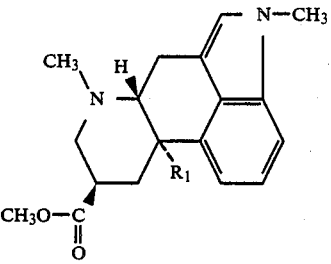

in which $R_1$ denotes a hydrogen atom or a methoxy group, which comprises reacting a methylating agent with a compound of formula:

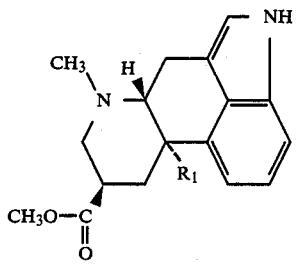

in which $R_1$ is defined as above, in the presence of a quaternary salt, in the presence of a solid metal alcoholate of formula $CH_3$—OM in which M denotes an alkali metal atom, or an alkali metal hydride, and in the presence of a dehydrating agent of formula $R_2$—COO—$CH_3$ in which $R_2$ denotes a hydrogen atom or an alkyl, alkyloxy, alkyloxycarbonyl or hydrocarbon aryl group or of formula $R_3$—$C(OCH_3)_3$ in which $R_3$ denotes a hydrogen atom, an alkyl group or a hydrocarbon aryl group.

2. A process according to claim 1, wherein the reaction is performed in an aprotic solvent which is an ether, ester or nitrile.

3. A process according to claim 1, wherein the dehydrating agent is methyl formate, methyl acetate, methyl benzoate, methyl carbonate, methyl oxalate or methyl orthoformate.

4. A process according to claim 1, wherein the quaternary salt is an ammonium salt or a phosphonium salt.

5. A process according to claim 1, wherein the methylating agent is a methyl halide, methyl sulphate, methyl methanesulphonate, methyl p-toluenesulphonate or methyl phosphate.

* * * * *